United States Patent
Han et al.

(10) Patent No.: US 12,427,117 B2
(45) Date of Patent: Sep. 30, 2025

(54) LIPID NANOPARTICLES MANUFACTURING CHIP, LIPID NANOPARTICLES MANUFACTURING SYSTEM HAVING THE SAME, AND LIPID NANOPARTICLES MANUFACTURING METHOD

(71) Applicant: Inventage Lab Inc., Gyeonggi-do (KR)

(72) Inventors: Euidon Han, Gyeonggi-do (KR); Chan Hee Chon, Gyeonggi-do (KR); Dong Hoon Kim, Gyeonggi-do (KR); Ju Hee Kim, Gyeonggi-do (KR)

(73) Assignee: INVENTAGE LAB INC., Gyeonggi-Do (KR)

( * ) Notice: Subject to any disclaimer, the term of this patent is extended or adjusted under 35 U.S.C. 154(b) by 0 days.

(21) Appl. No.: 18/024,743

(22) PCT Filed: May 11, 2022

(86) PCT No.: PCT/KR2022/006749
§ 371 (c)(1),
(2) Date: Mar. 3, 2023

(87) PCT Pub. No.: WO2022/240193
PCT Pub. Date: Nov. 17, 2022

(65) Prior Publication Data
US 2023/0285312 A1    Sep. 14, 2023

(30) Foreign Application Priority Data

May 11, 2021 (KR) .......... 10-2021-0060963
May 10, 2022 (KR) .......... 10-2022-0057190

(51) Int. Cl.
| | |
|---|---|
| A61K 9/51 | (2006.01) |
| B01F 23/40 | (2022.01) |
| B01F 23/41 | (2022.01) |
| B01F 23/451 | (2022.01) |
| B01F 23/80 | (2022.01) |
| B01F 33/301 | (2022.01) |
| B01L 3/00 | (2006.01) |
| C12N 15/88 | (2006.01) |
| B01F 101/22 | (2022.01) |

(52) U.S. Cl.
CPC .......... *A61K 9/5192* (2013.01); *A61K 9/5123* (2013.01); *B01F 23/4143* (2022.01); *B01F 23/4145* (2022.01); *B01F 23/451* (2022.01); *B01F 23/483* (2022.01); *B01F 23/49* (2022.01); *B01F 23/808* (2022.01); *B01F 33/3017* (2022.01); *B01L 3/502753* (2013.01); *C12N 15/88* (2013.01); *B01F 2101/22* (2022.01); *B01L 2200/16* (2013.01); *B01L 2300/0681* (2013.01); *B01L 2300/0883* (2013.01)

(58) Field of Classification Search
None
See application file for complete search history.

(56) References Cited

U.S. PATENT DOCUMENTS

| | | | |
|---|---|---|---|
| 2006/0087048 A1 | 4/2006 | Mello et al. | |
| 2010/0101953 A1* | 4/2010 | Yokoyama | B32B 3/26 210/651 |
| 2013/0175171 A1* | 7/2013 | Aizel | B01D 57/02 204/453 |
| 2013/0256134 A1* | 10/2013 | Han | B01L 3/502761 156/196 |
| 2017/0181972 A1 | 6/2017 | Hood et al. | |
| 2019/0271619 A1* | 9/2019 | Richards | B01L 3/502753 |

FOREIGN PATENT DOCUMENTS

| | | | | |
|---|---|---|---|---|
| JP | 2020-536230 A | 12/2020 | | |
| KR | 10-2017-0126944 A | 11/2017 | | |
| KR | 10-2020-0074832 A | 6/2020 | | |
| WO | WO-2011140627 A1 * | 11/2011 | ......... | A61K 31/7088 |
| WO | WO 2016/138175 A1 | 9/2016 | | |
| WO | WO 2019/070739 A1 | 4/2019 | | |

OTHER PUBLICATIONS

Kimura et al.; "Development of a Microfluidic-Based Post-Treatment Process for Size-Controlled Lipid Nanoparticles and Application to siRNA Delivery,"2020; American Chemical Socitey; ACS Applied Materials & Interfaces, vol. 12, pp. 34011-34020. (Year: 2020).*

Maeki et al.; "Advances in microfluidics for lipid nanoparticle and extracellular vesicles and applications in drug delivery systems," 2018; ELSEVIER; Advanced Drug Delivery Reviews, vol. 128, pp. 84-100. (Year: 2018).*

(Continued)

*Primary Examiner* — David J Blanchard
*Assistant Examiner* — Ivan A Greene
(74) *Attorney, Agent, or Firm* — The PL Law Group, PLLC

(57) ABSTRACT

A lipid nanoparticles manufacturing chip includes a mixer unit for forming a mixed solution by mixing a first raw material containing an active ingredient and a second raw material containing a lipid, a dilution unit that is connected to the mixer unit and dilutes the mixed solution using a diluent solution to make a diluted mixed solution, and a concentration unit connected to the dilution unit and for obtaining a concentrated solution by concentrating lipid nanoparticles (LNP) from the diluted mixed solution.

12 Claims, 12 Drawing Sheets

(56) References Cited

OTHER PUBLICATIONS

Salafi et al.; "Advancements in microfluidics for nanoparticle separation," 2017; RSC; Lab on a Chip, vol. 17, pp. 11-33. (Year: 2017).*
And kim et al.; "Nanofluidic concentration devices for biomolecules utilizing ion concentration polarization: theory, fabrication, and applications," 2010; RSC; Chemical Society Reviews, vol. 39, pp. 912-922. (Year: 2010).*
Lee et al.; "Multiplexed proteomic sample preconcentration device using surface-patterned ion-selective membrane," 2008; RSC; Lab on a Chip, vol. 8, pp. 596-601. (Year: 2008).*
Kim et al.; "Integration of nanoporous membranes into microfluidic devices: electrokinetic bio-sample pre-concentration," 2013, RSC; Analyst, vol. 138, pp. 6007-6015. (Year: 2013).*
Kimura et al.; "Development of a Microfluidic-Based Post-Treatment Process for Size Controlled Lipid Nanoparticles and Application to siRNA Delivery, "2020; American Chemical Society; ACS Applied Materials & Interfaces, vol. 12, pp. 34011-34020. (Year: 2020).*
Pawlowski et al.; "Computational fluid dynamics (CFD) assisted analysis of profiled membranes performance in reverse electrodialysis," 2016; ELSEVIER; Journal of Membrane Science, vol. 502, pp. 179-190. (Year: 2016).*
International Search Report for PCT/KR2022/006749 mailed on Aug. 12, 2022.
Office action issued on Jul. 6, 2022 from Korean Patent Office in a counterpart Korean Patent Application No. 10-2022-0057190 (English translation is also submitted herewith.).
Office action issued on Nov. 29, 2022 from Korean Patent Office in a counterpart Korean Patent Application No. 10-2022-0057190 (English translation is also submitted herewith.).
Notice of Allowance mailed on Jan. 19, 2023 from Korean Patent Office in a counterpart Korean Patent Application No. 10-2022-0057190 (English translation is also submitted herewith.).

* cited by examiner

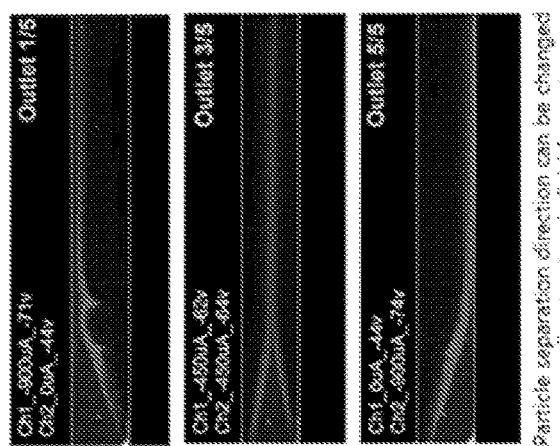
FIG. 7E
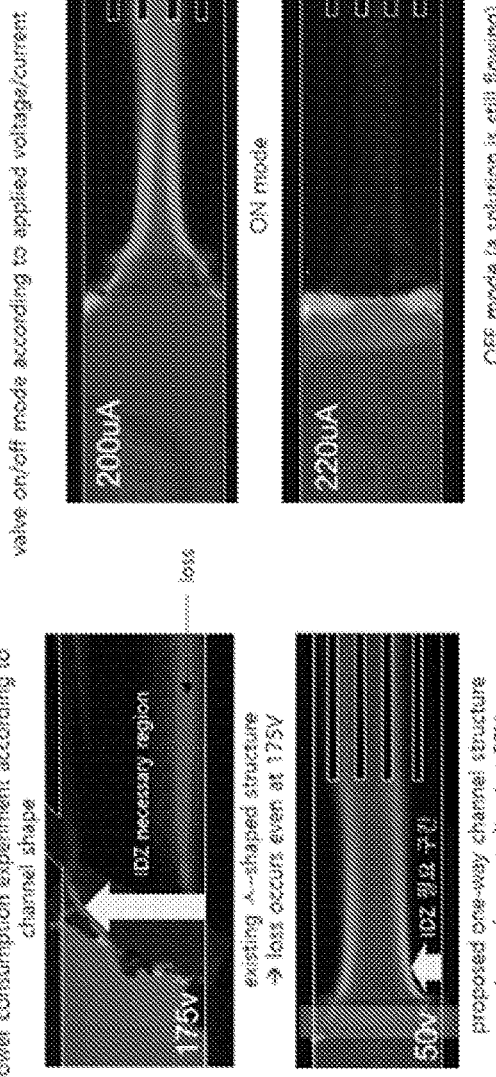
FIG. 7D
FIG. 7C

LIPID NANOPARTICLES MANUFACTURING CHIP, LIPID NANOPARTICLES MANUFACTURING SYSTEM HAVING THE SAME, AND LIPID NANOPARTICLES MANUFACTURING METHOD

CROSS REFERENCE TO RELATED APPLICATIONS AND CLAIM OF PRIORITY

This application claims benefit under 35 U.S.C. 119, 120, 121, or 365 (c), and is a National Stage entry from International Application No. PCT/KR2022/006749 filed on May 11, 2022, which claims priority to the benefit of Korean Patent Application Nos. 10-2021-0060963 filed on May 11, 2021 and 10-2022-0057190 filed on May 10, 2022 at the Korean Intellectual Property Office, the disclosures of which are incorporated by reference herein in their entirety.

BACKGROUND

1. Technical Field

The present invention relates to a lipid nanoparticles manufacturing chip, a lipid nanoparticles manufacturing system including the lipid nanoparticles manufacturing chip, and a lipid nanoparticles manufacturing method, and more particularly, it relates to a lipid nanoparticles manufacturing chip for manufacturing lipid nanoparticles containing active ingredients such as mRNA, a lipid nanoparticles manufacturing system having the lipid nanoparticles manufacturing chip, and a lipid nanoparticles manufacturing method containing the active ingredient.

2. Background Art mRNA (messenger RNA) is a material at the stage before protein synthesis, and contains genetic information. Since mRNA is accessible to various therapeutic agents, it can be used as a preventive or therapeutic vaccine, and proteins that are lacking can also be synthesized through mRNA. The advantage of mRNA therapeutics is that they do not have to be delivered to the nucleus compared to DNA, and they are not inserted into the genome, so they do not cause permanent genetic diseases, so they are highly safe. In addition, it is possible to synthesize even proteins that are lacking inside cells that are inaccessible to protein therapeutics with mRNA. mRNA can have various sizes depending on the protein it expresses, and exists as a single strand. mRNA made from DNA escapes from the nucleus into the cytoplasm and meets with ribosome to produce proteins. Although mRNA is in the limelight as a next-generation gene therapy, stability is very low because it is single-stranded. Therefore, it is known that it is rapidly degraded by nucleases in the blood, rapidly excreted out of the body through the kidneys, and does not easily pass through cell membranes due to its strong negative charge.

In the treatment using anionic drugs including nucleic acids, safe and efficient drug delivery technologies have been studied for a long time, and various delivery systems and delivery technologies have been developed. Various studies related to mRNA vaccines using a method of encapsulating and delivering mRNA in lipid nanoparticles are being conducted, and research on mass production systems for this is ongoing.

Recently, in fields such as pharmaceuticals, vaccines, and DDS (drug delivery systems), a method of encapsulating and delivering mRNA in lipid nanoparticles has been in the limelight, but there are difficulties in mass production. There is a bulk manufacturing method in which turbulence is generated in a large container to mix, dilute, and concentrate, but it is difficult to obtain uniform quality of the manufactured lipid nanoparticles and it is difficult to control the manufacturing process.

SUMMARY

Accordingly, the technical problem of the present invention has been conceived in this respect, and an object of the present invention is to provide a lipid nanoparticles manufacturing chip for producing lipid nanoparticles.

Another object of the present invention is to provide a lipid nanoparticles manufacturing system including the lipid nanoparticles manufacturing chip.

Another object of the present invention is to provide a lipid nanoparticles manufacturing method.

According to an exemplary embodiment of the inventive concept, a lipid nanoparticles manufacturing chip includes a mixer unit for forming a mixed solution by mixing a first raw material containing an active ingredient and a second raw material containing a lipid, a dilution unit that is connected to the mixer unit and dilutes the mixed solution using a diluent solution to make a diluted mixed solution, and a concentration unit connected to the dilution unit and for obtaining a concentrated solution by concentrating lipid nanoparticles (LNP) from the diluted mixed solution.

In an embodiment of the present invention, the concentration unit includes a main flow path connected to the dilution unit, an ion exchange channel in contact with the main flow path, a buffer solution channel spaced apart from the main flow path and in contact with the ion exchange channel, a lipid nanoparticle acquisition flow path connected to the main flow path and obtaining the concentrated solution, and a collecting flow path connected to the main flow path and collecting a solution other than the concentrated solution.

In an embodiment of the present invention, the ion exchange channel of the concentration unit is disposed above or below the main flow path and has a v-shape such that a sharp point of the v-shape is disposed in a flow direction of a fluid.

In an embodiment of the present invention, the lipid nanoparticle acquisition flow path and the collecting flow path have a smaller cross-sectional area than that of the main flow path and are disposed parallel to each other.

In an embodiment of the present invention, the mixer unit includes a first raw material supply flow path through which the first raw material is supplied, a second raw material supply flow path through which the second raw material is supplied, and a mixing flow path connected to the first and second raw material supply flow paths.

In an embodiment of the present invention, the dilution unit includes a first flow path connected to the mixing flow path of the mixer unit, a dilution flow path providing the diluent solution, and a dilution space connected to the dilution flow path and the first flow path.

In an embodiment of the present invention, the active ingredient is a nucleic acid.

In an embodiment of the present invention, the active ingredient is any one of mRNA, miRNA, siRNA, DNA and CRISPR.

In an embodiment of the present invention, the first raw material includes mRNA and water, the second raw material includes lipid and ethanol, and the diluent solution includes deionized water.

According to an exemplary embodiment of the inventive concept, a lipid nanoparticles manufacturing system includes a first raw material supply unit for supplying a first raw material, a second raw material supply unit for supplying a second raw material, a lipid nanoparticles manufacturing chip including a mixer unit mixing the first raw material and the second raw material to form a mixed solution, a dilution unit for diluting the mixed solution, and a concentration unit for obtaining a concentrated solution by concentrating lipid nanoparticles from the diluted mixed solution, a diluent solution providing unit for providing a diluent solution to the lipid nanoparticles manufacturing chip, and a collecting unit for collecting solutions other than the concentrated solution from the lipid nanoparticles manufacturing chip.

In an embodiment of the present invention, the concentration part of the lipid nanoparticles manufacturing chip includes a main flow path connected to the dilution unit, an ion exchange channel in contact with the main flow path, a buffer solution channel spaced apart from the main flow path and in contact with the ion exchange channel, a lipid nanoparticle acquisition flow path connected to the main flow path and obtaining the concentrated solution, and a collecting flow path connected to the main flow path and collecting a solution other than the concentrated solution.

In an embodiment of the present invention, the ion exchange channel of the concentration unit of the lipid nanoparticles manufacturing chip is disposed above or below the main flow path and has a v-shape so that a sharp point of the v-shape is disposed in a flow direction of a fluid.

In an embodiment of the present invention, the dilution unit of the lipid nanoparticles manufacturing chip includes a first flow path connected to the mixer unit, a dilution flow path providing the diluent solution, and a dilution space connected to the dilution flow path and the first flow path.

According to an exemplary embodiment of the inventive concept, a lipid nanoparticles manufacturing method includes a step of preparing a first raw material including an active ingredient and a second raw material including lipid, a step of forming lipid nanoparticles including the active ingredient by mixing the first raw material and the second raw material, and a post-processing step of producing a final product by filtering a solution including the lipid nanoparticles and filling the solution which is filtered into an individual container. And the step of forming lipid nanoparticles is performed on a lipid nanoparticles manufacturing chip in which a flow path is formed, and includes a mixing step of mixing the first raw material and the second raw material to form a mixed solution, a dilution step of diluting the mixed solution using a diluent solution to make a diluted mixed solution, and a concentration step of obtaining a concentrated solution by concentrating lipid nanoparticles from the diluted mixed solution.

In an embodiment of the present invention, in the concentration step of the step of forming lipid nanoparticles, a voltage is applied to a buffer solution channel connected to an ion exchange channel in contact with the flow path of the lipid nanoparticles manufacturing chip, an ion enrichment zone and an ion depletion zone are formed in the solution within the flow path, and thus lipid nanoparticles containing active ingredient are concentrated in a specific area within the flow path.

In an embodiment of the present invention, the lipid nanoparticles manufacturing chip includes a mixer unit mixing the first raw material and the second raw material to form the mixed solution, a dilution unit that is connected to the mixer unit and dilutes the mixed solution using the diluent solution, and a concentration unit connected to the dilution unit and concentrating the lipid nanoparticles from the diluted mixed solution.

In an embodiment of the present invention, the concentration unit of the lipid nanoparticles manufacturing chip includes a main flow path connected to the dilution unit, an ion exchange channel in contact with the main flow path, a buffer solution channel spaced apart from the main flow path and in contact with the ion exchange channel, a lipid nanoparticle acquisition flow path connected to the main flow path and obtaining the concentrated solution, and a collecting flow path connected to the main flow path and collecting a solution other than the concentrated solution.

According to the exemplary embodiments of the present invention, since mixing, dilution, and concentration for lipid nanoparticle manufacturing are all performed on a lipid nanoparticles manufacturing chip, it is easy to control the size and uniformity of lipid nanoparticles, and thus high quality lipid nanoparticles can be manufactured.

However, the effects of the present invention are not limited to the above effects and may be variously expanded without departing from the spirit and scope of the present invention.

BRIEF DESCRIPTION OF THE DRAWINGS

FIGS. 7A to 7E are views for explaining the fluid flow and concentrating effect according to the shape of the ion exchange unit of an embodiment of a lipid nanoparticles manufacturing chip.

DETAILED DESCRIPTION

Figure 1:
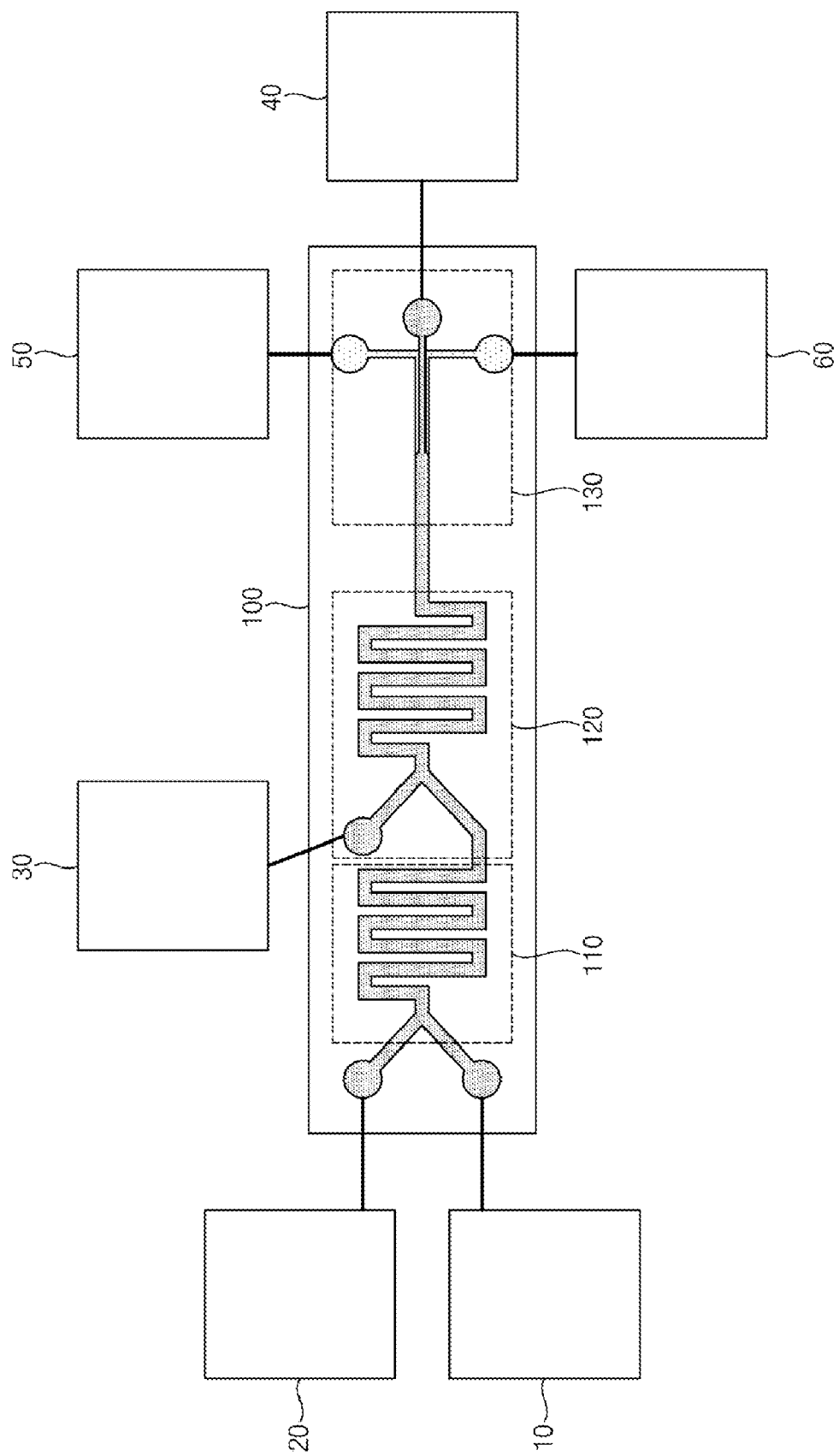
FIG. 1 is a schematic diagram of a lipid nanoparticles manufacturing system according to an embodiment of the present invention.

Hereinafter, exemplary embodiments of the present invention will be described in more detail with reference to the drawings.

Since the present invention may have various changes and have various forms, specific exemplary embodiments are illustrated in the drawings and described in detail in the text. However, it is not intended to limit the present invention to the specific disclosed form, and it will be appreciated that the present invention includes all modifications, equivalences, or substitutions included in the spirit and the technical scope of the present invention.

Figure 2A:
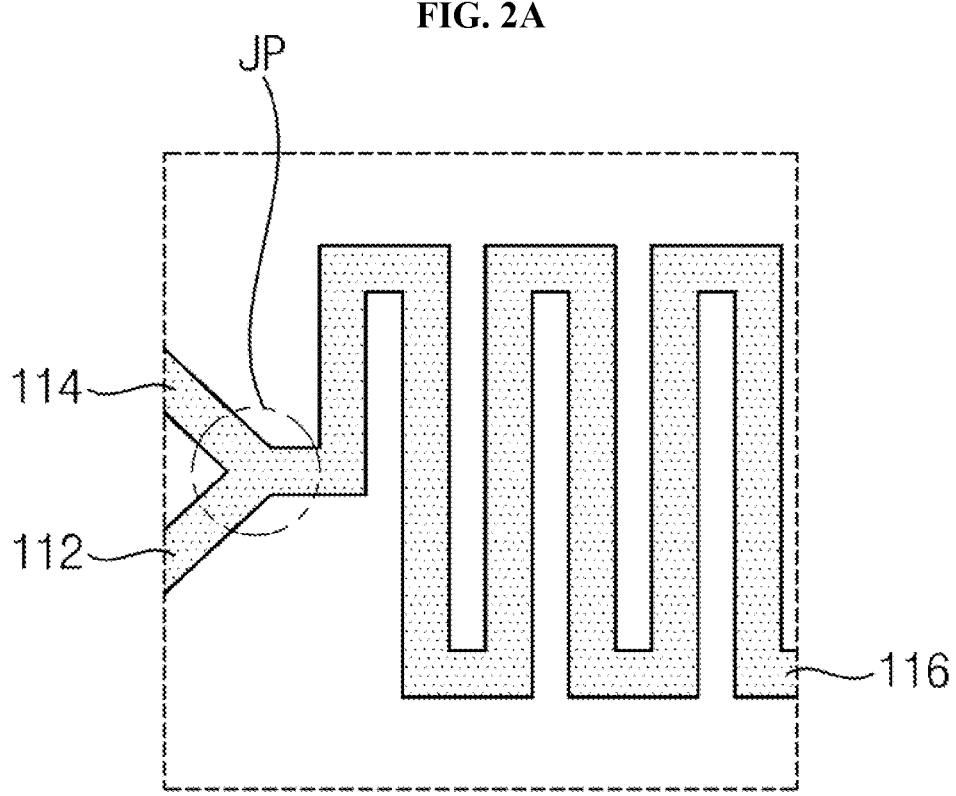
FIGS. 2A and 2B are views illustrating various examples of a mixer unit of a lipid nanoparticles manufacturing chip of a lipid nanoparticle manufacturing system of FIG. 1.
Figure 2B:
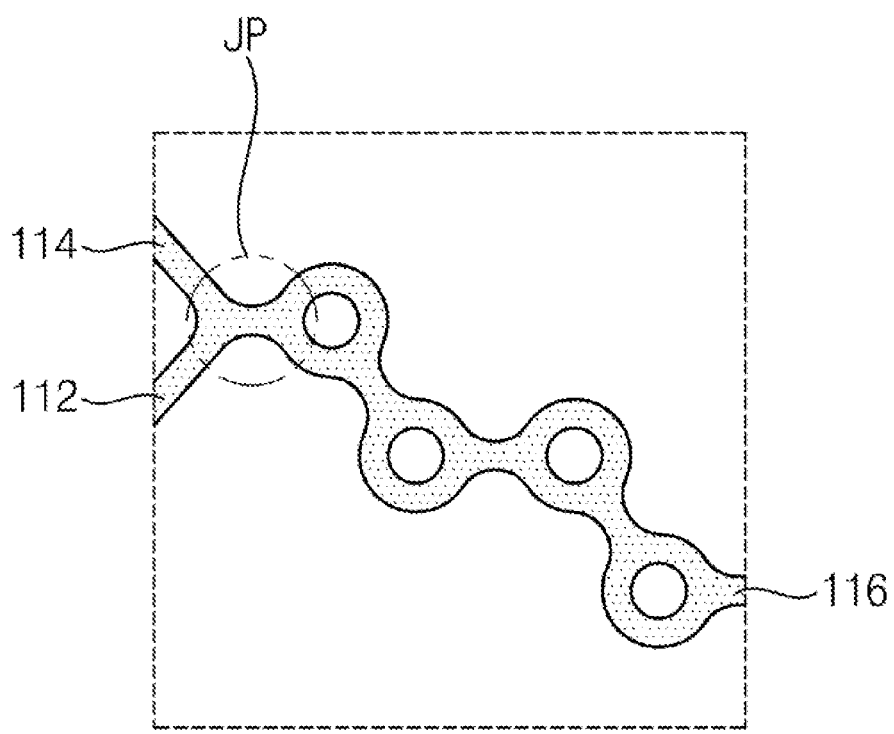
Figure 3A:
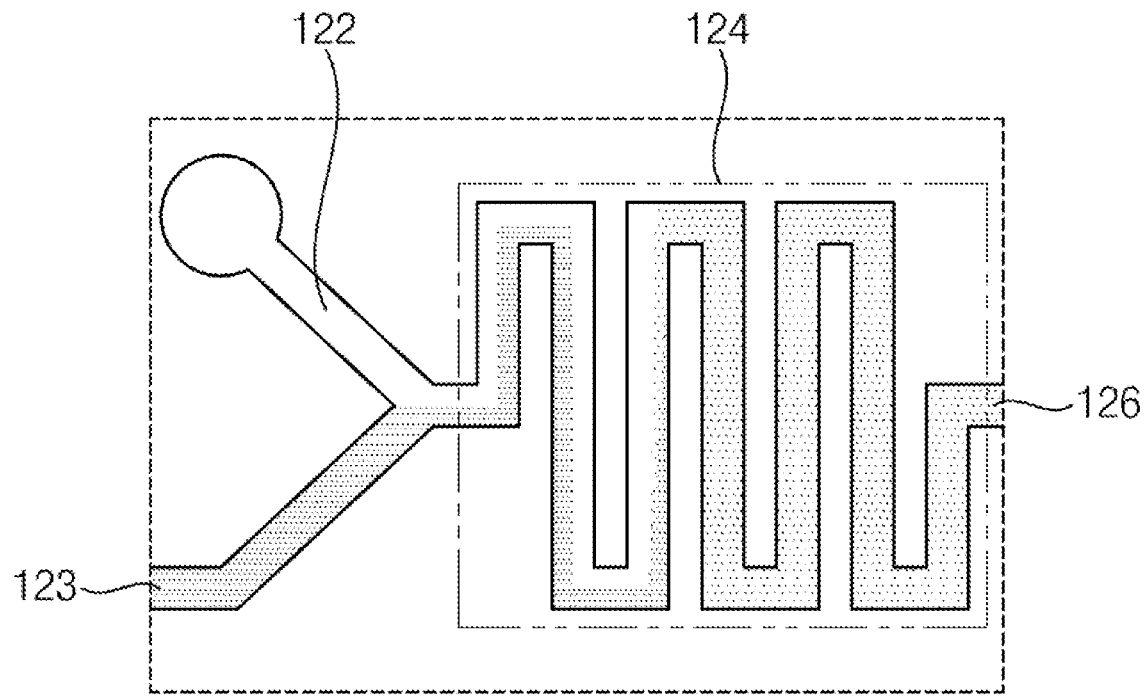
FIGS. 3A and 3B are views illustrating various examples of a dilution unit of a lipid nanoparticles manufacturing chip of a lipid nanoparticle manufacturing system of FIG. 1.
Figure 3B:
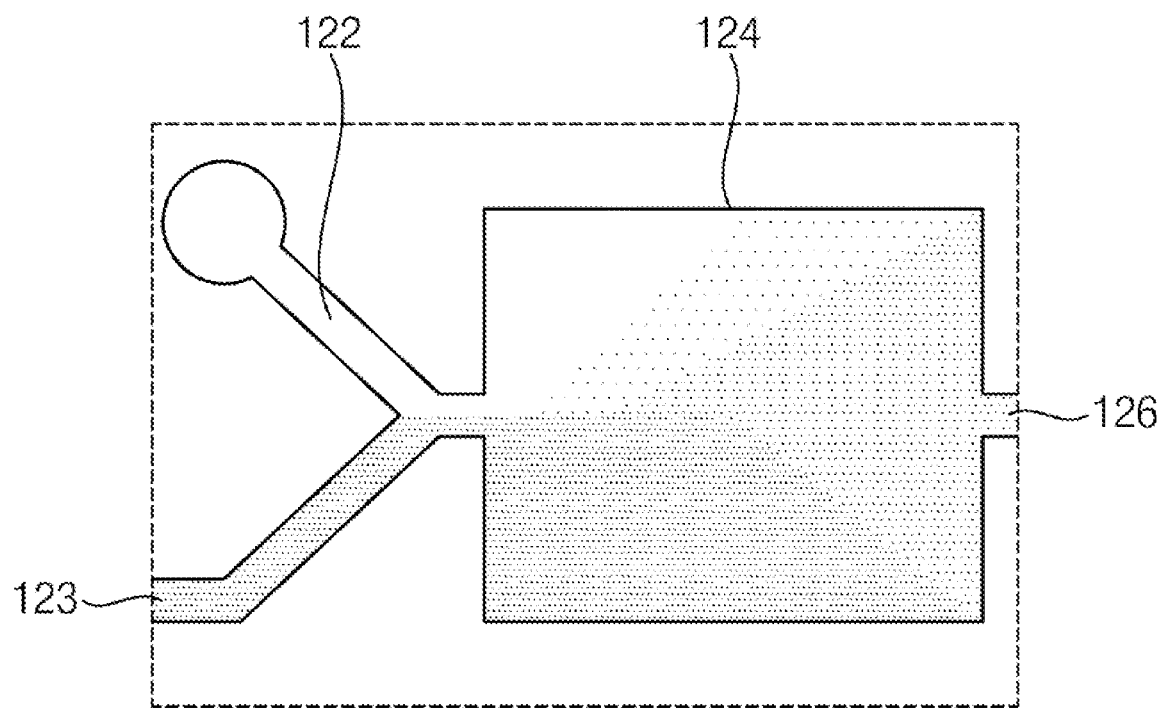
Figure 4A:
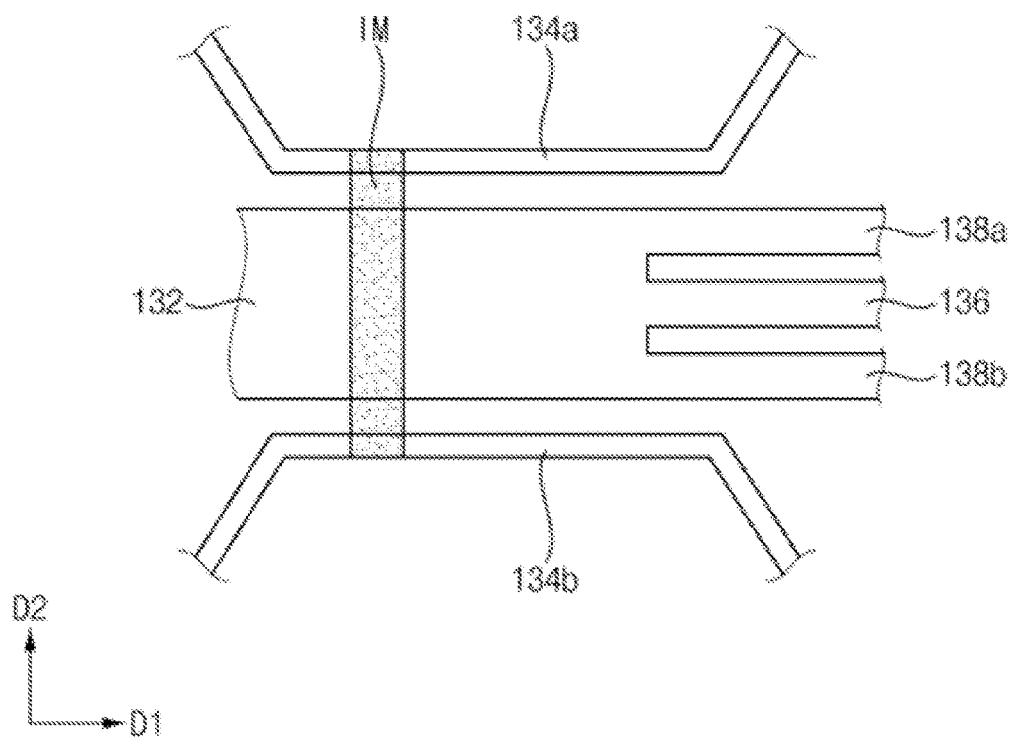
FIGS. 4A and 4B are views for explaining a concentration unit of a lipid nanoparticles manufacturing chip of a lipid nanoparticle manufacturing system of FIG. 1.
Figure 4B:
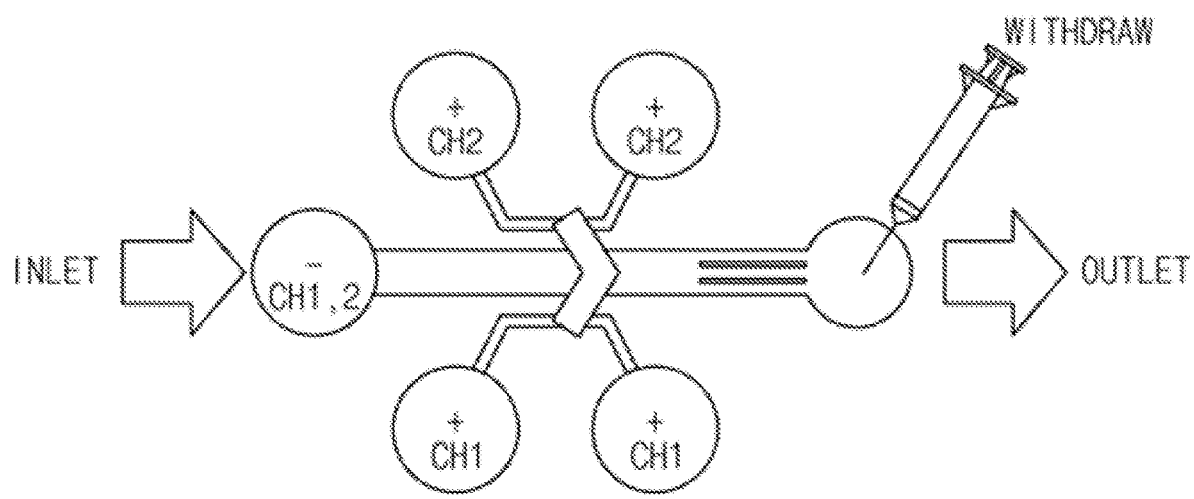

FIG. 1 is a schematic diagram of a lipid nanoparticles manufacturing system according to an embodiment of the present invention. FIGS. 2A and 2B are views illustrating various examples of a mixer unit of a lipid nanoparticles manufacturing chip of a lipid nanoparticle manufacturing system of FIG. 1. FIGS. 3A and 3B are views illustrating various examples of a dilution unit of a lipid nanoparticles manufacturing chip of a lipid nanoparticle manufacturing system of FIG. 1. FIGS. 4A and 4B are views for explaining a concentration unit of a lipid nanoparticles manufacturing chip of a lipid nanoparticle manufacturing system of FIG. 1.

Referring to FIGS. 1 to 4B, the lipid nanoparticle manufacturing system includes a first raw material supply unit 10 including mRNA, a second raw material supply unit 20 including lipid, a diluent solution providing unit 30, a lipid nanoparticle acquisition unit 40, a first collecting unit 50, a second collecting unit 60, and a lipid nanoparticle manufacturing chip 100.

The first raw material supply unit 10 stores the first raw material and supplies the first raw material to the lipid nanoparticle manufacturing chip 100. The first raw material may be a solution containing mRNA. For example, the first raw material may include mRNA and water.

The second raw material supply unit 20 stores the second raw material and supplies the second raw material to the lipid nanoparticle manufacturing chip 100. The second raw material may be a solution containing lipid. For example, the second raw material may include lipid and ethanol.

The lipid nanoparticle manufacturing chip 100 may mix, dilute, and concentrate the first raw material and the second raw material to prepare a lipid nanoparticle concentrated solution containing mRNA. The lipid nanoparticle manufacturing chip 100 includes a mixer unit 110, a dilution unit 120, and a concentration unit 130.

The mixer unit 110 may prepare a mixed solution by mixing the first raw material and the second raw material. As the mixer unit 110, a microfluidic mixer commonly used in a microchannel, such as a chaotic mixer or a herringbone mixer, may be used. At this time, a mixed solution containing lipid nanoparticles can be prepared by self-aligning of lipids and mRNA at the interface of the two fluids through mixing of the first raw material and the second raw material in the flow path.

For example, the mixer unit 110 includes a first raw material supply flow path 112 through which the first raw material is supplied, a second raw material supply flow path 114 through which the second raw material is supplied, and a mixing flow path 116 connected to the first and second raw material supply flow paths. The first raw material supply flow path 112 and the second raw material supply flow path 114 meet each other at the merging point JP so that the first raw material and the second raw material may be mixed.

The dilution unit 120 may dilute the mixed solution. The dilution unit 120 may include a first flow path 123 connected to the mixing flow path 116 of the mixer unit 110, a dilution flow path 122 providing the diluent solution, and a dilution space 124 connected to the dilution flow path 122 and the first flow path 123. The dilution space 124 may have various shapes, such as a line shape (see FIG. 3A), a serpentine chamber shape (see FIG. 3B), and the like. The diluent solution providing unit 30 may provide the diluent solution to make a diluted mixed solution through the dilution flow path 122 of the dilution unit 120 of the lipid nanoparticle manufacturing chip 100. The diluent may include deionized water.

Since the solution mixed in the mixer unit 110 contains a high concentration of the solvent of the second raw material, such as ethanol, dilution is required to a desired concentration. The concentration of the ethanol may be lowered to a desired level while passing through the dilution unit 120.

Although not shown, the dilution unit 120 may be implemented in the flow path structure of the mixer unit 110. That is, a mixing dilution unit is configured so that the mixer unit and the dilution unit are not sequentially configured, but are implemented at the same time, and a structure in which the first raw material, the second raw material, and the diluent solution are input is also possible.

The concentration unit 130 may concentrate the lipid nanoparticles from the mixed solution diluted in the dilution unit 120 to obtain a concentrated solution. The concentration unit 130 may include a main flow path 132 connected to the dilution unit 120, an ion exchange channel IM in contact with the main flow path 132, buffer solution channels 134a and 134b spaced apart from the main flow path 132 and in contact with the ion exchange channel IM, a lipid nanoparticle acquisition flow path 136 connected to the main flow path 132 and obtaining the concentrated solution, and collecting flow paths 138a and 138b connected to the main flow path 132 and recovering solutions other than the concentrated solution. The ion exchange channel IM may be a charged nanochannel for exchanging cations or anions made of a nanoporous material.

In the concentration unit 130, lipid nanoparticles having a size of 100 nm or less may be separated and concentrated using an ion concentration polarization (ICP) phenomenon.

ICP phenomenon refers to a natural phenomenon in which, when a channel is located on both sides with the ion exchange membrane in the middle and a voltage is applied to both ends of the channel, in the case of a cation exchange channel, an ion enrichment zone is formed as cations move to an ion exchange membrane, and an ion depletion zone (IDZ) is formed on the relatively opposite side. The ion depletion zone generates a strong repulsive force to push ions/molecules regardless of polarity, and lipid nanoparticles can be separated and concentrated using this.

According to the present embodiment, buffer solution channels 134a and 134b through which buffer solutions flow may be formed at both sides of the second direction D2 of the main flow path 132 through which fluid flows along the first direction D1, respectively. When an appropriate voltage is applied to both buffer solution channels 134a and 134b, ions move through the ion exchange channel IM, and an ion depletion zone (refer to IDZ of FIG. 7C) may be formed on both sides of the main flow path 132 along the second direction D2. Thus, lipid nanoparticles having an electrodense core are concentrated in the center of the main flow path 132 and pass through the lipid nanoparticle acquisition flow path 136. That is, the cation component is used as a driving source of the ion concentration polarization phenomenon and is discharged to the outside of the chip through the main flow path 132 and the ion exchange channel IM through the buffer solution channels 134a and 134b. The remaining cationic component may be influenced by an electric field formed at the ion-deficient zone and the interface of the ion-deficient zone to selectively move through the lipid nanoparticle acquisition flow path 136 and the collecting flow paths 138a and 138b according to the nature of the particles.

Accordingly, the concentration of lipid nanoparticles increases in the fluid passing through the lipid nanoparticle acquisition flow path 136, and fluids other than the lipid nanoparticles can be recovered in the collecting flow paths 138a and 138b.

According to an embodiment of the present invention, mixing to prepare lipid nanoparticles, dilution to dilute a solvent such as ethanol, and concentration to increase lipid nanoparticle concentration can all be performed on the lipid nanoparticle manufacturing chip 100.

The ion exchange channel IM may have various shapes (see FIGS. 5A to 5E and 6A and 6B). For example, the ion exchange channel IM is disposed above or below the main flow path 132 and may have an I-shape on a plane or a V-shape such that a sharp point of the v-shape is disposed in a flow direction of a fluid.

A sum of widths of the collecting flow paths 138a and 138b in the second direction D2 may be smaller than the width of the main flow path 132. For example, the collecting flow paths 138a and 138b may have an I-shaped channel structure as a whole since the main flow path 132 is divided into three flow paths and formed in parallel. The area occupied by the concentration unit 130 is reduced, compared to a structure in which flow paths are radially formed, space integration efficiency is improved, and fluid flow is improved, and thus production efficiency may be improved because it can be driven even with low power. In addition, the same or superior efficiency can be obtained with lower power consumption compared to the conventional structure in which the ion depletion zone is generated on both sides and the ion depletion zone is formed only on one side of the flow path, and it can be used as an on/off valve by adjusting the power (see FIG. 7D).

Meanwhile, in this embodiment, a structure in which the main flow path is divided into three branches, including one lipid nanoparticle acquisition flow path and two collecting flow paths, is described, but is not limited thereto. For example, the main flow path may be divided into 5 or 7 branches, and the size and width of each of the divided flow paths may be different.

Here, the lipid nanoparticle manufacturing chip 100 may be manufactured by various known methods. For example, it may be formed by stacking a plurality of substrates having grooves corresponding to flow paths. For example, an ion exchange channel may be formed on a lower substrate, and an upper substrate having a groove formed on a lower surface may be formed by bonding to the lower substrate, but is not limited thereto. As for the material of the substrate, various substrates capable of forming a flow path pattern such as a glass substrate, a plastic substrate, and a silicon substrate may be used. In order to form the flow path pattern, various known methods such as an etching method, a laser engraving method, an imprint method, and a photolithography method may be used. For bonding of the plurality of substrates, various known methods such as a laser bonding method, a thermal compression method, an adhesion method, and a lamination method may be used.

According to the present invention, since mixing, dilution, and concentration for lipid nanoparticle manufacturing are all performed on a lipid nanoparticle manufacturing chip (on chip process), the fluid can be controlled in a laminar flow state. Accordingly, it is easy to control the size and uniformity of the lipid nanoparticles, and thus high-quality lipid nanoparticles can be manufactured. According to the bulk size manufacturing method, which cannot control turbulence, fine fluid control is impossible, and thus it is difficult to control the size and uniformity of lipid nanoparticles. In the conventional lipid nanoparticle manufacturing method using the chip method, only mRNA and lipid are mixed on the chip, and the steps for diluting an organic solvent such as ethanol, and concentrating lipid nanoparticles are all performed in a bulk size through a separate process. Therefore, it is not easy to control the manufacturing process of lipid nanoparticles compared to the present invention.

In particular, in the case of a solution containing lipid nanoparticles in an early stage manufactured in a microfluidics chip, ethanol of a specific concentration must be included according to flow ratio conditions in the manufacturing stage, in particular, the Flow Rate Ratio between Aqueous Phase and Organic Phase where lipids are dissolved in ethanol. Since the concentration of ethanol contained is an unstable state that can affect the lipid of nanoparticles in the early stages, the application of effective post-processing has a great influence on the production of stable lipid nanoparticles. Through the bulk size process, in some cases, lipid nanoparticles at an early stage are discharged to the outside of the chip and do not maintain stability until diluted in bulk size through a tubing line. However, according to embodiments of the present invention, since mixing, dilution, and concentration of lipid nanoparticles are all performed on a chip (on chip process), this problem can be solved.

FIGS. 5A to 5E are views illustrating various examples of a concentration unit of a lipid nanoparticles manufacturing chip of a lipid nanoparticle manufacturing system of FIG. 1.

Figure 5A:
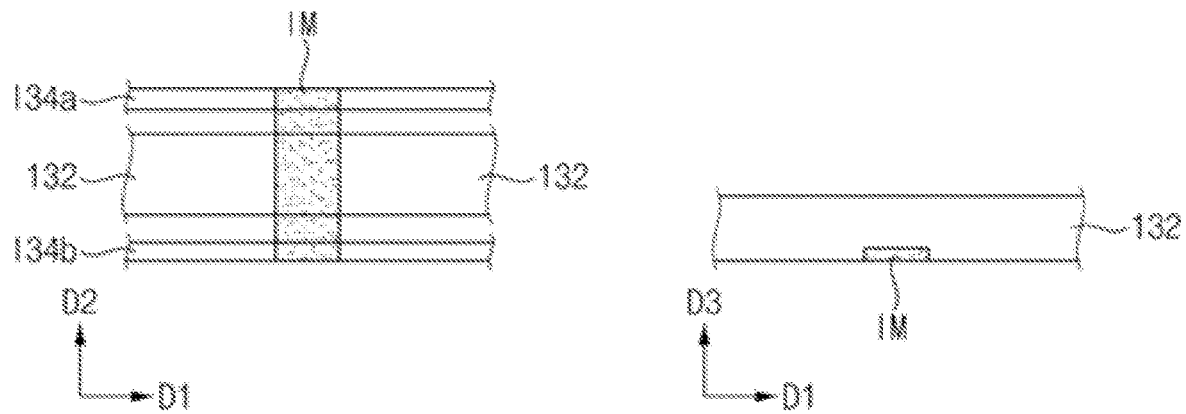
FIGS. 5A to 5E are views illustrating various examples of a concentration unit of a lipid nanoparticles manufacturing chip of a lipid nanoparticle manufacturing system of FIG. 1.

FIG. 5A shows a case in which the ion exchange channel IM has an I-shape extending in a second direction D2 perpendicular to the first direction D1 in which the main flow path 132 extends. When viewed from a side surface, the ion exchange channel IM may be formed on a lower side surface of the main flow path 132 to have a predetermined height in a third direction D3 perpendicular to the first and second directions D1 and D2.

Meanwhile, other configurations of the concentration unit are omitted since the configuration of the concentration unit described above is substantially the same.

Figure 5B:
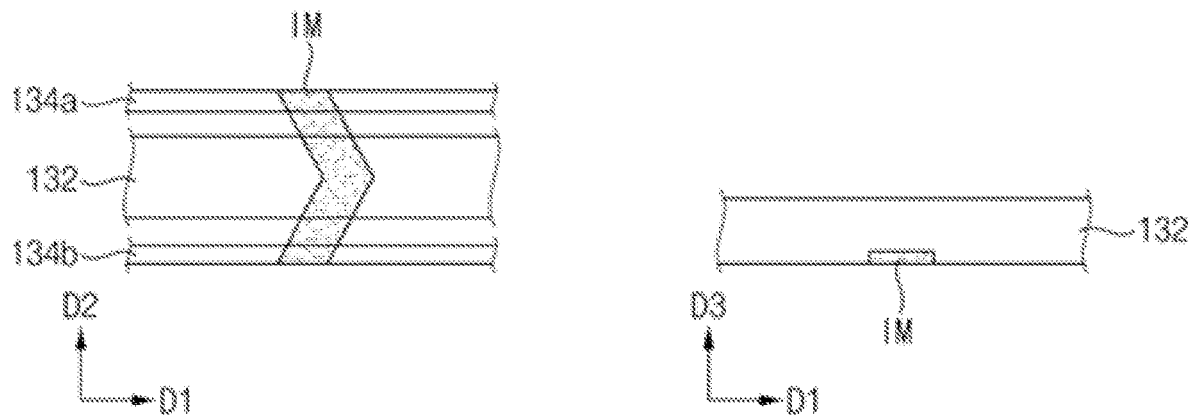
Figure 5C:
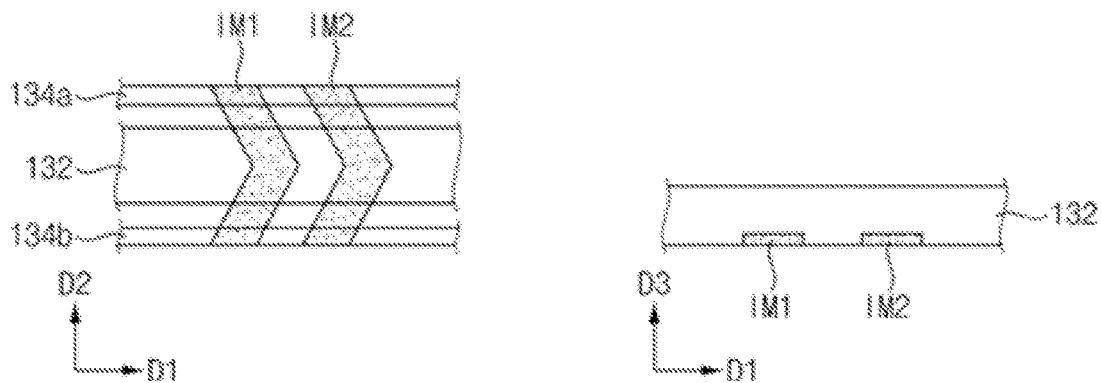
Figure 5D:
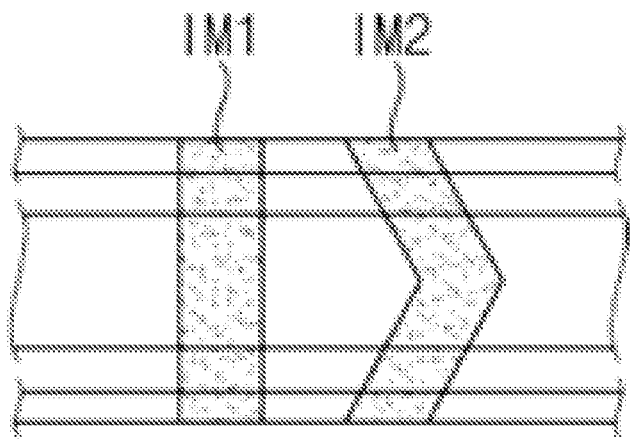
Figure 5E:
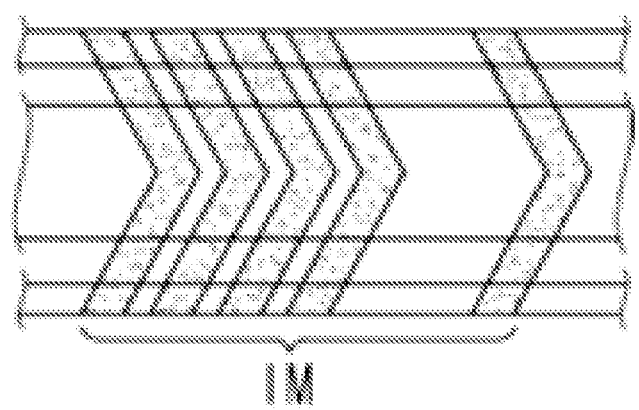

FIG. 5B illustrates an embodiment in which an ion exchange channel IM is formed in a V-shape, FIG. 5C illustrates an embodiment in which two V-shaped ion exchange channels IM1 and IM2 are formed, FIG. 5D illustrates an embodiment in which an I-shaped ion exchange channel IM1 and a V-shaped ion exchange channel IM2 are sequentially formed, and FIG. 5E illustrates an embodiment in which a plurality of V-shaped ion exchange channels IM are formed.

Figure 6A:
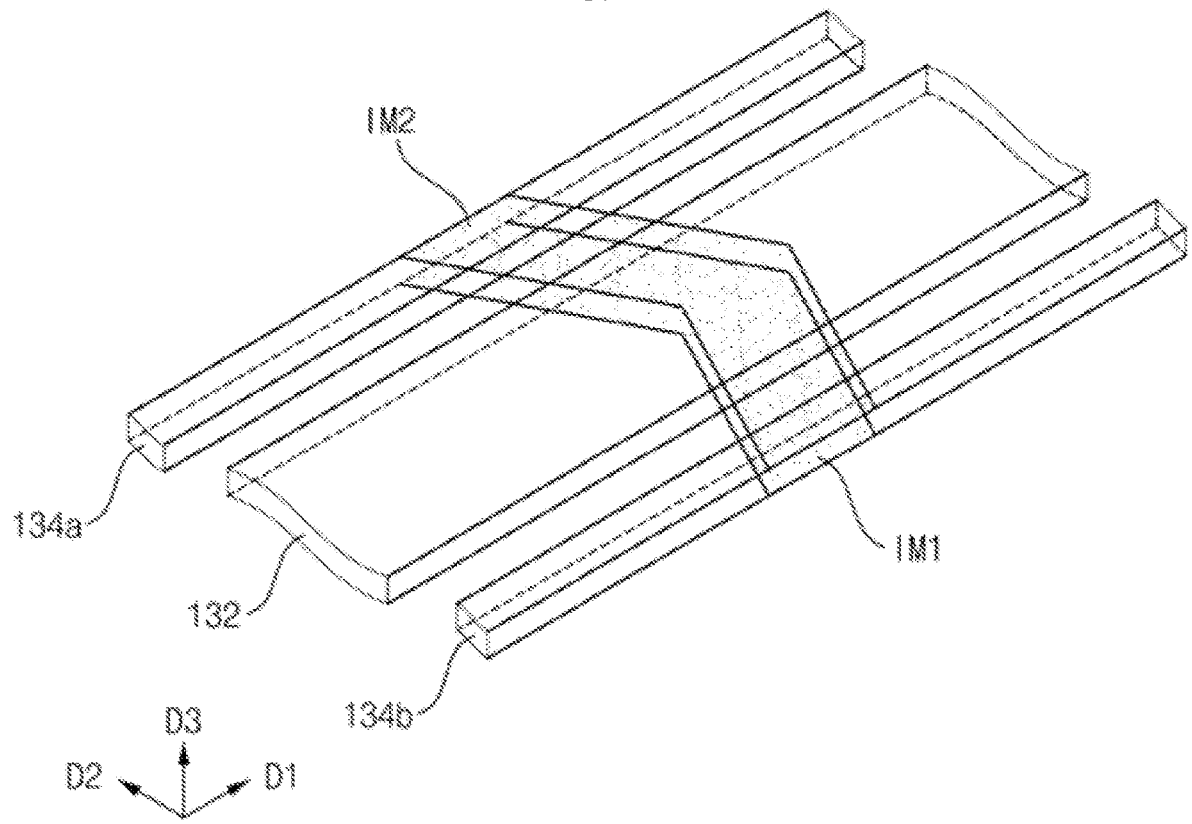
FIGS. 6A and 6B are views illustrating an embodiment of a concentration unit of a lipid nanoparticles manufacturing chip of a lipid nanoparticle manufacturing system of FIG. 1.
Figure 6B:
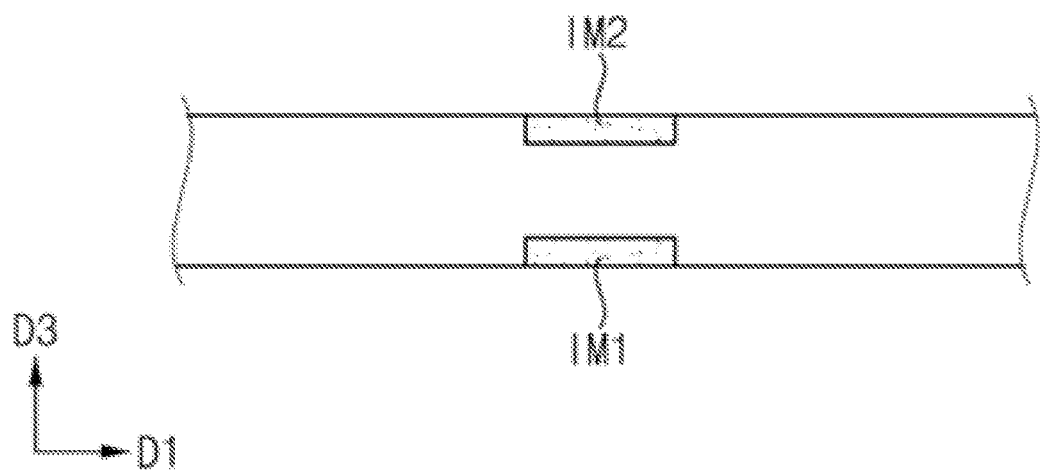

FIGS. 6A and 6B are views illustrating an embodiment of a concentration unit of a lipid nanoparticles manufacturing chip of a lipid nanoparticle manufacturing system of FIG. 1.

Referring to FIGS. 6A and 6B when viewed from the side, the ion exchange channels IM1 and IM2 are formed on the upper and lower surfaces of the main flow path 132, and the ion depletion zone can be formed more efficiently.

FIGS. 7A to 7E are views for explaining the fluid flow and concentrating effect according to the shape of the ion exchange unit of an embodiment of a lipid nanoparticles manufacturing chip.

Referring to FIGS. 7A to 7E, it can be confirmed that the concentration effect is maximized and power consumption is reduced when the ion exchange membrane has a V-shape rather than an I-shape.

Figure 7A:
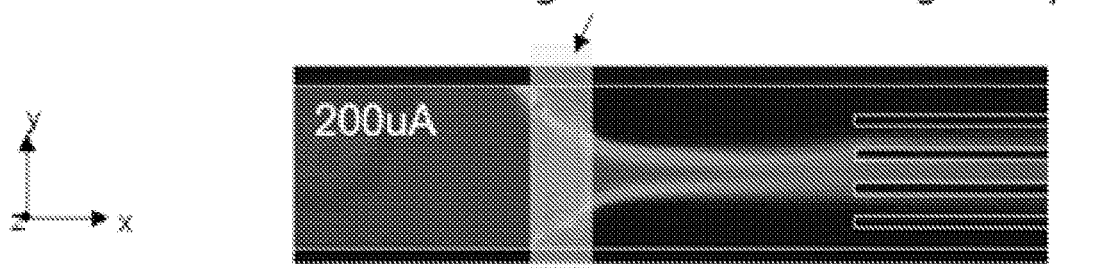
Figure 7A:
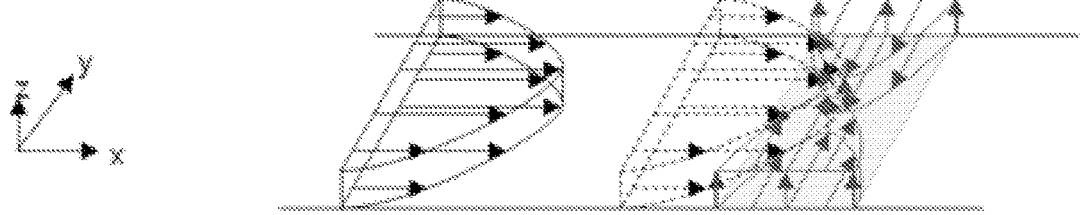
Figure 7A:
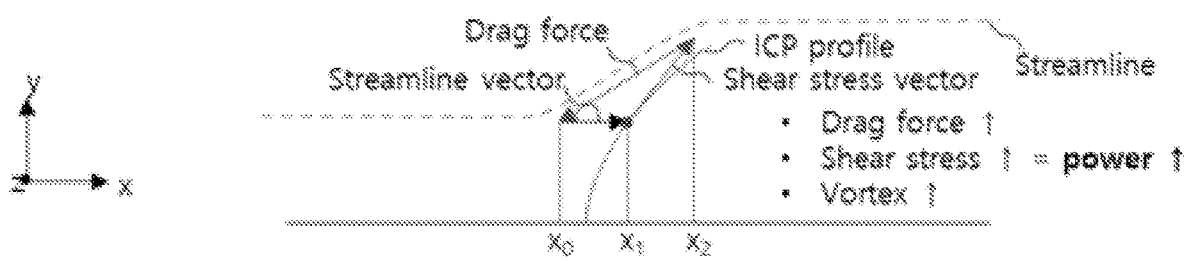
Figure 7B:
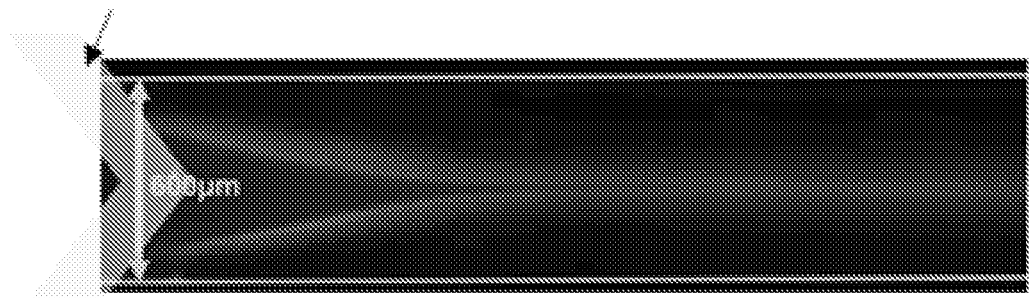
Figure 7B:
Figure 7B:
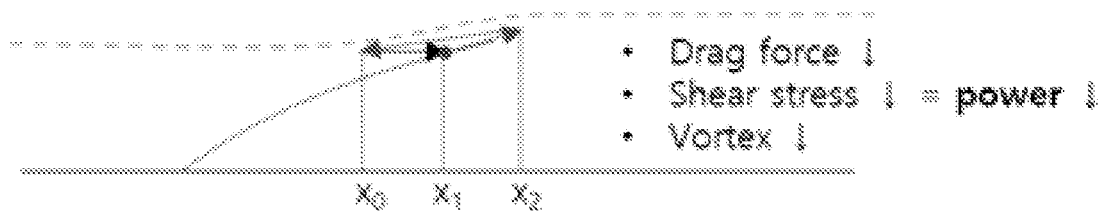

FIG. 7A is a diagram illustrating the fluid flow and concentrating effect of the I-shaped ion exchange channel, and FIG. 7B is a diagram illustrating the fluid flow and concentrating effect of the V-shaped ion exchange channel.

FIG. 7C is the result of the power consumption comparison experiment according to the channel shape. FIG. 7D is a view illustrating an experiment confirming that whether lipid nanoparticles are concentrated (valve effect) can be controlled according to an applied voltage/current. FIG. 7E is a view illustrating an experiment confirming that the particle separation direction can be changed according to the formation of an electric field.

According to FIGS. 7C to 7E, the concentration unit of the lipid nanoparticles manufacturing chip according to an embodiment of the present invention not only functions to concentrate lipid nanoparticles, but also controls the obtained lipid nanoparticles in the form of an on/off valve. If necessary, it is possible to control to obtain necessary particles not only through the lipid nanoparticle acquisition flow path but also through the collecting flow path.

Figure 8:
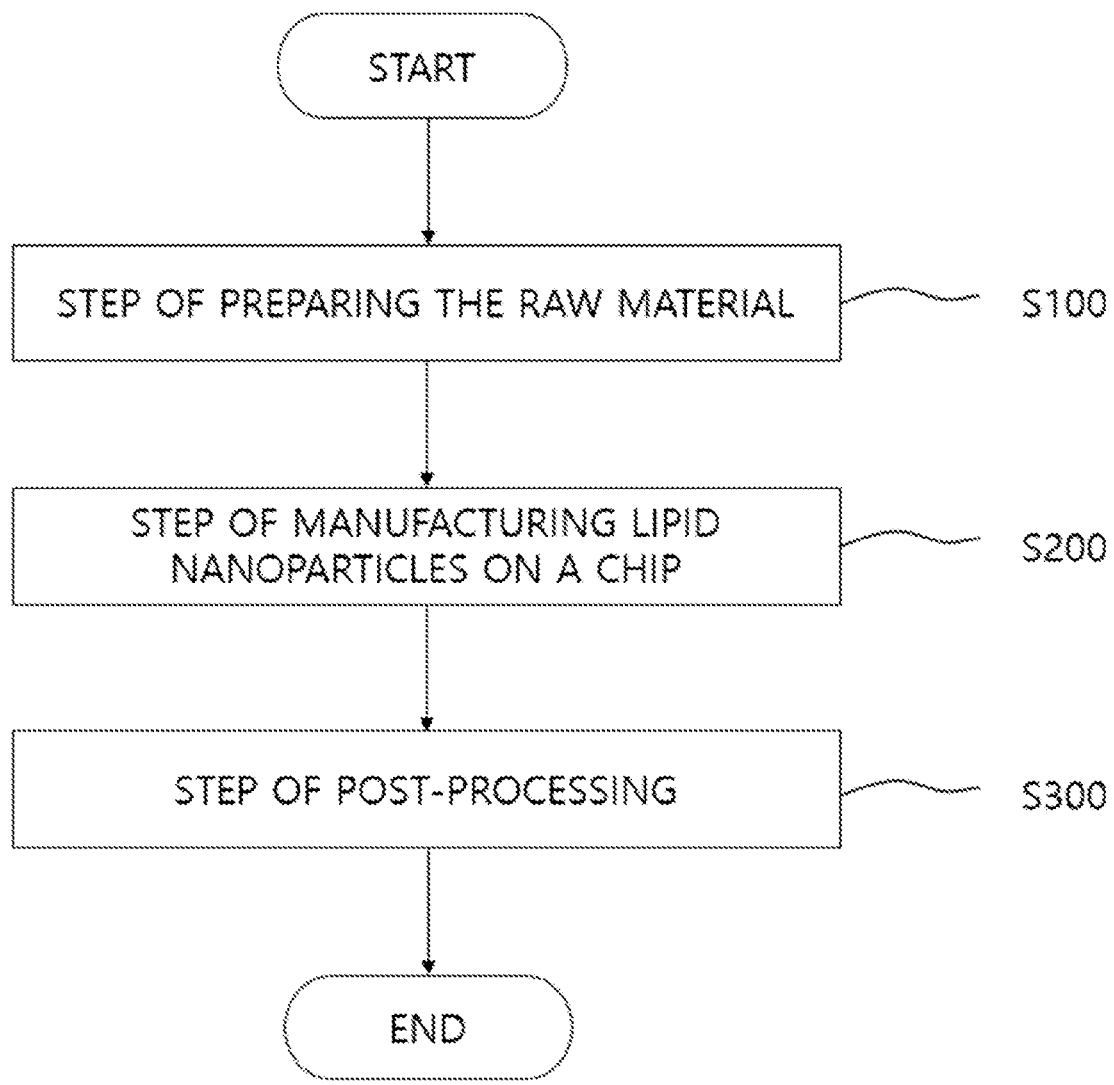
FIG. 8 is a flowchart illustrating a lipid nanoparticles manufacturing method according to an embodiment of the present invention.
Figure 9:
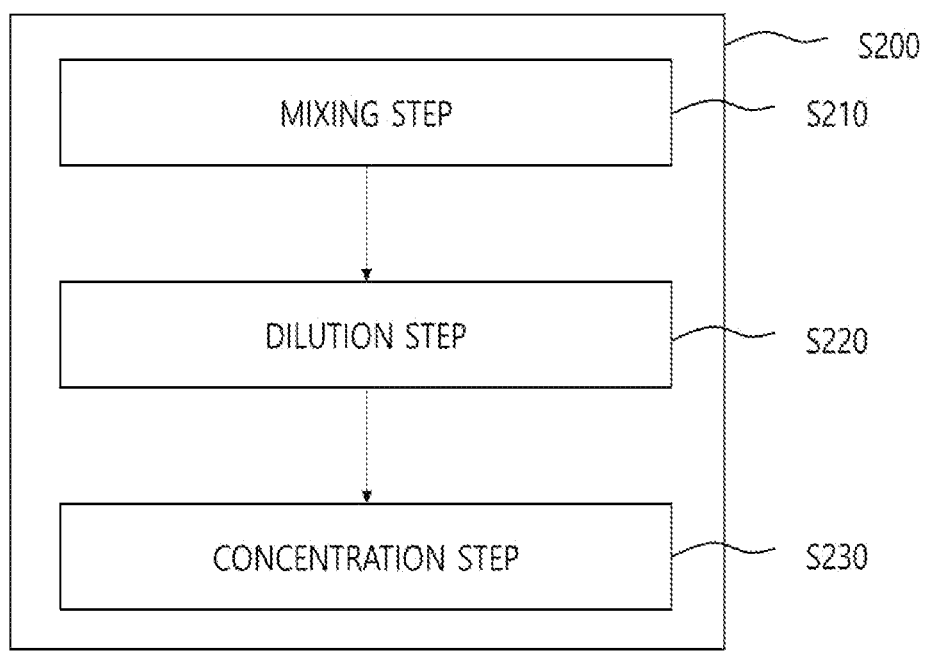
FIG. 9 is a flowchart illustrating in detail the steps of preparing LNPs on a chip in a lipid nanoparticles manufacturing method of FIG. 8.

FIG. 8 is a flowchart illustrating a lipid nanoparticles manufacturing method according to an embodiment of the present invention. FIG. 9 is a flowchart illustrating in detail the steps of preparing lipid nanoparticles on a chip of a lipid nanoparticles manufacturing method of FIG. 8.

Referring FIGS. 8 and 9, the lipid nanoparticles manufacturing method may include a step of preparing raw materials S100, a step of manufacturing lipid nanoparticles on a chip S200, and a step of post-processing S300.

In the step of preparing the raw material S100, a first raw material including mRNA and a second raw material including lipid may be prepared.

In the step of manufacturing lipid nanoparticles on a chip S200, lipid nanoparticles containing mRNA may be formed by mixing the first raw material and the second raw material.

In the step of post-processing S300, the final product may be produced by diafiltration of the solution containing the lipid nanoparticles, additional concentration to a required concentration, and filling into individual containers.

At this time, the step of manufacturing lipid nanoparticles on a chip S200 is performed on a lipid nanoparticles manufacturing chip on which a flow path is formed, and may include a mixing step S210, a dilution step S220, and a concentration step S230. The lipid nanoparticles manufacturing chip may be a lipid nanoparticles chip described in FIG. 1 and the like. For example, the lipid nanoparticles manufacturing chip may include a mixer unit, a dilution unit, and a concentration unit.

In the mixing step S210, a mixed solution may be formed by mixing the first raw material and the second raw material. The mixing step S210 may be performed in the mixer unit of the lipid nanoparticles manufacturing chip.

In the dilution step S220, the mixed solution may be diluted using a diluent solution. The dilution step S220 may be performed in the dilution unit of the lipid nanoparticles manufacturing chip.

In the concentration step S230, a concentrated solution may be obtained by concentrating the lipid nanoparticles from the diluted mixed solution. The concentration step S230 may be performed in the concentration unit of the lipid nanoparticles manufacturing chip. Specifically, the concentrated solution applies a voltage to a buffer solution channel connected to an ion exchange channel in contact with the flow path of the lipid nanoparticles manufacturing chip, and forms an ion enrichment zone and an ion depletion zone in the solution within the flow path, and thus lipid nanoparticles containing mRNA can be concentrated in a specific area within the flow path.

Although the present invention has been described with reference to the above exemplary embodiments, it will be understood by those skilled in the art that various modifications and changes may be made to the present invention without departing from the spirit and scope of the present invention as set forth in the claims below:

What is claimed is:

1. A lipid nanoparticles manufacturing chip comprising:
a mixer unit for forming a mixed solution by mixing a first raw material containing an active ingredient and a second raw material containing a lipid;
a dilution unit that is connected to the mixer unit and dilutes the mixed solution using a diluent solution to make a diluted mixed solution; and
a concentration unit connected to the dilution unit and for obtaining a concentrated solution by concentrating lipid nanoparticles (LNP) from the diluted mixed solution,
wherein the mixer unit, the dilution unit and the concentration unit are formed on one substrate; and
the concentration unit comprises:
a main flow path connected to the dilution unit, wherein the diluted mixed solution flows in one direction;
an ion exchange channel in contact with the main flow path;
a buffer solution channel spaced apart from the main flow path and in contact with the ion exchange channel, wherein a voltage is applied to a buffer solution of the buffer solution channel to form an ion enrichment zone and an ion depletion zone in a solution within the main flow path, wherein the diluted mixed solution is separated into the concentrated solution and a solution other than the concentrated solution on the main flow path by the ion exchange channel and the buffer solution channel to which a voltage is applied;
wherein, at a position after the diluted mixed solution on the main flow path is passed through the ion exchange channel and separated into the concentrated solution and the solution other than the concentrated solution, the main flow path is divided, into:
a lipid nanoparticle acquisition flow path connected downstream to the mainflow path and configured for obtaining the concentrated solution flowing in the one direction; and
a collecting flow path connected downstream to the main flow path and configured for collecting the solution other than the concentrated solution flowing in the one direction,
wherein the concentrated solution and the solution other than the concentrated solution are simultaneously and continuously obtained and collected.

2. The lipid nanoparticles manufacturing chip of claim 1, wherein the ion exchange channel of the concentration unit is disposed above or below the main flow path and has a v-shape such that a sharp point of the v-shape is disposed in a flow direction of a fluid.

3. The lipid nanoparticles manufacturing chip of claim 1, wherein the lipid nanoparticle acquisition flow path and the collecting flow path have a smaller cross-sectional area than that of the main flow path and are disposed parallel to each other.

4. The lipid nanoparticles manufacturing chip of claim 1, wherein the mixer unit comprises a first raw material supply flow path through which the first raw material is supplied, a second raw material supply flow path through which the second raw material is supplied, and a mixing flow path connected to the first and second raw material supply flow paths.

5. The lipid nanoparticles manufacturing chip of claim 4, wherein the dilution unit comprises:

a first flow path connected to the mixing flow path of the mixer unit;

a dilution flow path providing the diluent solution; and a dilution space connected to the dilution flow path and the first flow path.

6. The lipid nanoparticles manufacturing chip of claim 1, wherein the active ingredient is a nucleic acid.

7. The lipid nanoparticles manufacturing chip of claim 1, wherein the active ingredient is any one of mRNA, miRNA, siRNA, DNA and CRISPR.

8. The lipid nanoparticles manufacturing chip of claim 1, wherein the first raw material comprises mRNA and water, the second raw material comprises lipid and ethanol, and the diluent solution comprises deionized water.

9. A lipid nanoparticles manufacturing system comprising:

a first raw material supply unit for supplying a first raw material;

a second raw material supply unit for supplying a second raw material;

the lipid nanoparticles manufacturing chip of claim 1;

a diluent solution providing unit for providing a diluent solution to the lipid nanoparticles manufacturing chip; and a collecting unit for collecting solutions other than the concentrated solution from the lipid nanoparticles manufacturing chip.

10. The lipid nanoparticles manufacturing system of claim 9, wherein the ion exchange channel of the concentration unit of the lipid nanoparticles manufacturing chip is disposed above or below the main flow path and has a v-shape so that a sharp point of the v-shape is disposed in a flow direction of a fluid.

11. The lipid nanoparticles manufacturing system of claim 9, wherein the dilution unit of the lipid nanoparticles manufacturing chip comprises:

a first flow path connected to the mixer unit;

a dilution flow path providing the diluent solution; and a dilution space connected to the dilution flow path and the first flow path.

12. A lipid nanoparticles manufacturing method comprising:

preparing a first raw material comprising an active ingredient and a second raw material comprising lipid;

forming lipid nanoparticles comprising the active ingredient by mixing the first raw material and the second raw material; and producing a final product by filtering a solution comprising the lipid nanoparticles and filling the solution which is filtered into an individual container, and wherein the forming of the lipid nanoparticles is performed on the lipid nanoparticles manufacturing chip of claim 1, and the forming of the lipid nanoparticles comprises:

mixing the first raw material and the second raw material to form a mixed solution;

diluting the mixed solution using a diluent solution to make a diluted mixed solution; and concentrating lipid nanoparticles from the diluted mixed solution to obtain a concentrated solution.

\* \* \* \* \*